US005549506A

United States Patent [19]
Higa et al.

[11] Patent Number: 5,549,506
[45] Date of Patent: Aug. 27, 1996

[54] APPARATUS FOR SUPPORTING AND CONTAINING A DENTAL PROSTHESIS DURING THE MICRO-ETCHING THEREOF

[76] Inventors: Jack Higa, 974 Esquimalt Avenue, West Vancouver, British Columbia, Canada, V7T 1J8; Lawrence R. Higa, 2932 Fulton St., San Franciso, Calif. 94188

[21] Appl. No.: 369,469

[22] Filed: Jan. 6, 1995

[51] Int. Cl.⁶ .............................. B24C 9/00; B24B 41/06
[52] U.S. Cl. .......................... 451/89; 451/387; 451/391; 451/404; 451/453; 451/87
[58] Field of Search .............................. 451/87, 89, 365, 451/366, 387, 391, 404, 451, 453

[56] References Cited

U.S. PATENT DOCUMENTS

| | | | |
|---|---|---|---|
| 834,067 | 10/1906 | Loughman et al. | |
| 882,363 | 3/1908 | Wright | 451/365 X |
| 2,059,039 | 10/1936 | Sandman | 451/453 |
| 2,153,476 | 4/1939 | Norman | 451/365 X |
| 2,491,957 | 12/1949 | Dilley | 451/451 X |
| 4,300,318 | 11/1981 | Brown | 451/89 X |
| 4,656,995 | 4/1987 | Merwin | 451/453 X |
| 4,787,179 | 11/1988 | Lewis | 451/89 |
| 4,918,873 | 4/1990 | Bass | 451/87 X |

*Primary Examiner*—Timothy V. Eley
*Attorney, Agent, or Firm*—Shlesinger, Arkwright & Garvey

[57] ABSTRACT

Apparatus for supporting and containing a dental prosthesis during the micro-etching thereof is disclosed. The apparatus includes a framework, a holding mechanism carried by the framework for holding the prosthesis in a position which permits micro-etching, and a flexible hood, for example, a disposable plastic bag, which has an open end sized to slidably receive the framework into the hood while holding the prosthesis. The open end is sealable while the framework is so received, and the hood is transparent to permit viewing of the prosthesis within the hood. The hood is sliceable with a knife edge to provide a small slit which permits the tip of a micro-etching tool to extend into the hood. Alternately, the hood may be pre-slit for the same purpose.

14 Claims, 4 Drawing Sheets

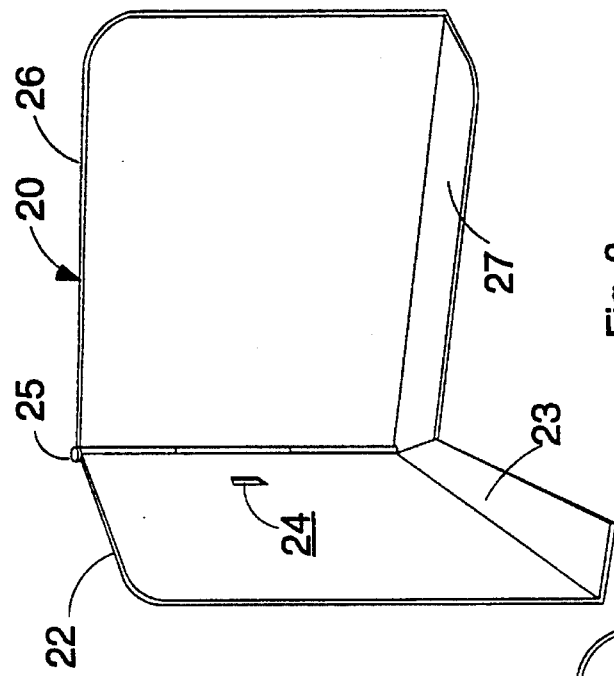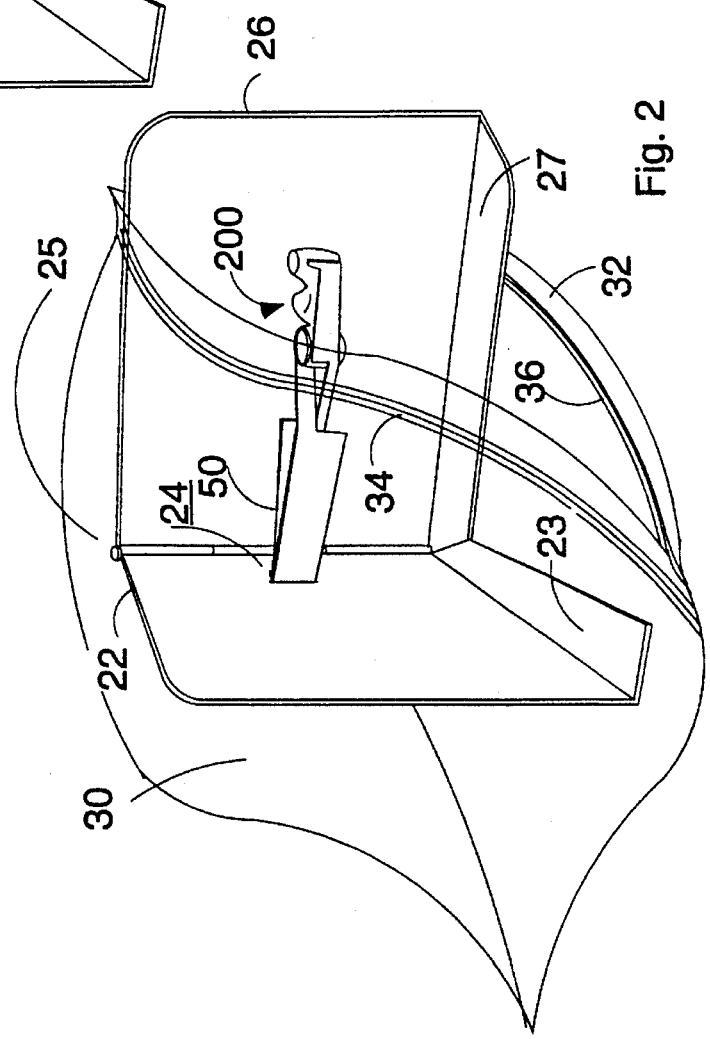

APPARATUS FOR SUPPORTING AND CONTAINING A DENTAL PROSTHESIS DURING THE MICRO-ETCHING THEREOF

FIELD OF THE INVENTION

This invention relates to dentistry, and in particular to containers used to collect dust or other particles which scatter or spray during the micro-etching of a dental prosthesis.

BACKGROUND TO THE INVENTION

In the field of dentistry, micro-etching is a well established procedure. It involves the use of a high pressure air stream of particles such as aluminum oxide or the like to bombard the surface of a prosthesis and produce micro-pitting of the surface. As well, a cleansing action is performed. The pitted or micro-etched surface exhibits increased irregularities and protuberances which serve to increase the effective surface area of the prosthesis and to enhance its bonding characteristics over that of a smooth surface. Used in combination with appropriate dental adhesives and cements, the micro-etching procedure enables the strength of a bond between a dental crown and a tooth preparation to be improved remarkably.

Micro-etching is a messy procedure. The high pressure stream of etching particles, mixed with etched particles, rebounds or scatters from the material surface and at times may miss the surface entirely if the operator's aim veers away. The result is a dusty atmosphere of fine particles and micro-organisms which can drift over a considerable area unless contained. However, even when the atmosphere is contained, the container itself becomes dirty and unsanitary.

A typical container designed for use during the micro-etching of dental prostheses is the Model DC-1 dust cabinet manufactured or supplied by Danville Engineering Inc. of San Ramon, Calif. It is a box-like structure which has a hinged top to allow access for cleaning, a raised perforated floor to trap waste particles, a pair of front openings to permit the operator to introduce and hold a prosthesis with one hand and a micro-etching tool with the other, and a perforated interior back wall which again serves as a form of trap and stands in advance of a fan or vacuum system designed to draw dust through a removable filter assembly in the exterior back wall of the cabinet. The hinged top includes a replaceable acrylic window to allow viewing of operations within the cabinet. Interior lighting is provided to enhance such viewing. Each hand opening is cuffed or guarded with flexible slitted material which permits a hand to enter the cabinet, then engages around the wrist to limit particles from exiting back through the opening.

Danville also provides a smaller, more compact version of their Model DC-1 dust cabinet. This is their Model MC dust cabinet described as the "Dentist Model". The basic feature of the Model MC cabinet which distinguishes it from the Model DC-1 cabinet is recognition that it should not be necessary to place one's entire hands into a cabinet merely to work on a prosthesis such as a crown or bridge. All that needs to go in the cabinet is the fingers of one hand to hold the crown or bridge and the micro-etching tip, the tool being held outside by the other hand, to do the micro-etching. Consequently, the cabinet can be made smaller.

Whether large or small, such cabinets are relatively complex, consisting of many parts, and are relatively expensive. Further, they are relatively cumbersome-more more so in the case of larger models. In addition, the maintenance of sanitary conditions is a problem. This is exemplified by the need for filters and fan or vacuum systems, and perforated interior floors and walls to trap particles. But, effectiveness is limited, and the cabinet interiors still require frequent cleaning to maintain sanitary conditions. While the hinged tops permit access for this purpose, the job of cleaning is still a time consuming task. Moreover, it can be a particularly difficult task when the objective is to clean all parts, surfaces and corners not only of etching particles but also micro-organisms.

Accordingly, a primary object of the present invention is to provide a new and improved container for supporting and containing a dental prosthesis during micro-etching of the prosthesis, a container which not only serves to effectively contain particles and micro-organisms, but also which has only limited cleaning requirements and is easy to clean to the extent that cleaning is required.

A further object of the present invention is to provide a micro-etching container for a dental prosthesis which is relatively inexpensive, simple in structure, and easy to use.

SUMMARY OF THE INVENTION

In a broad aspect of the present invention, there is provided apparatus for supporting and containing a dental prosthesis during the micro-etching thereof, the apparatus comprising a framework, holding means carried by the framework for holding the prosthesis in a position which permits micro-etching, and a flexible, enclosing hood which has an open end for slidably receiving the framework into the hood while holding the prosthesis. The framework is configured to hold the hood away from contact with the prosthesis while the framework is so received.

The open end of the hood is sealable while the framework is so received, and the hood is transparent to permit viewing of the prosthesis within the hood. The hood is sliceable with a knife edge to provide a small slit which permits the tip of a micro-etching tool to extend into the hood. Alternately, the hood may be pre-slit for such purpose.

The framework and holding means of such apparatus may be constructed very simply with a few small components. These components can be quickly and completely cleaned, if necessary using a sterilizing bath to kill micro-organisms. Rigid box-like dust cabinets, including light fixtures, fan or vacuum assemblies and the like, are not easily susceptible to such cleaning, and are avoided with the present invention.

The hood can be as simple as a transparent plastic bag of suitable dimensions. Once used, the bag does not require cleaning—it is a low cost throw away item which carries particles and micro-organisms away when it is thrown away.

The entire structure can be made small and compact to the point where an operator may hold the apparatus in one hand while manipulating a micro-etching tool with the other. This enables the process of micro-etching a prosthesis to be expedited at the side of a dental patient rather than at some distance away at a desk, counter or the like. Since the means for holding the prosthesis is carried by the framework, neither the operator's hands or fingers are exposed to the micro-etching environment within the bag during the process.

In a preferred embodiment, the holding means comprises a holder for releasably gripping the prosthesis, and the apparatus includes means for removably attaching the holder to the framework. The holder is then easily replaceable and may be cleaned independently of the framework.

Advantageously, the framework is collapsible between an open working position and a storage position. It may comprise a first segment for carrying the holding means and a second segment hingedly connected with the first segment.

The foregoing and other features and advantages of the present invention will now be described with reference to the drawings.

BRIEF DESCRIPTION OF THE DRAWINGS

FIG. 2 is a perspective view illustrating the apparatus of FIG. 1 with the hood partially slipped on.

FIG. 3 is a perspective view of the framework in the apparatus of FIG. 1 when standing in a working position.

DETAILED DESCRIPTION

FIGS. 1 to 6 illustrate apparatus and parts thereof in accordance with the present invention for supporting and containing a dental prosthesis during the micro-etching of the prosthesis. The best overview may be seen in FIG. 1 which shows the apparatus generally designated 10 ready to be used for the micro-etching of a dental bridgework generally designated 200 with a micro-etching tool generally designated 300.

Bridgework 200 is not part of the invention. It appears in the Figures only by way of example and merely for the purpose of illustration. The same is true for micro-etching tool 300. Such tools are widely used and available from a number of sources. The tool depicted in FIG. 1 is merely illustrative of such tools and is not part of the invention.

Figure 1:
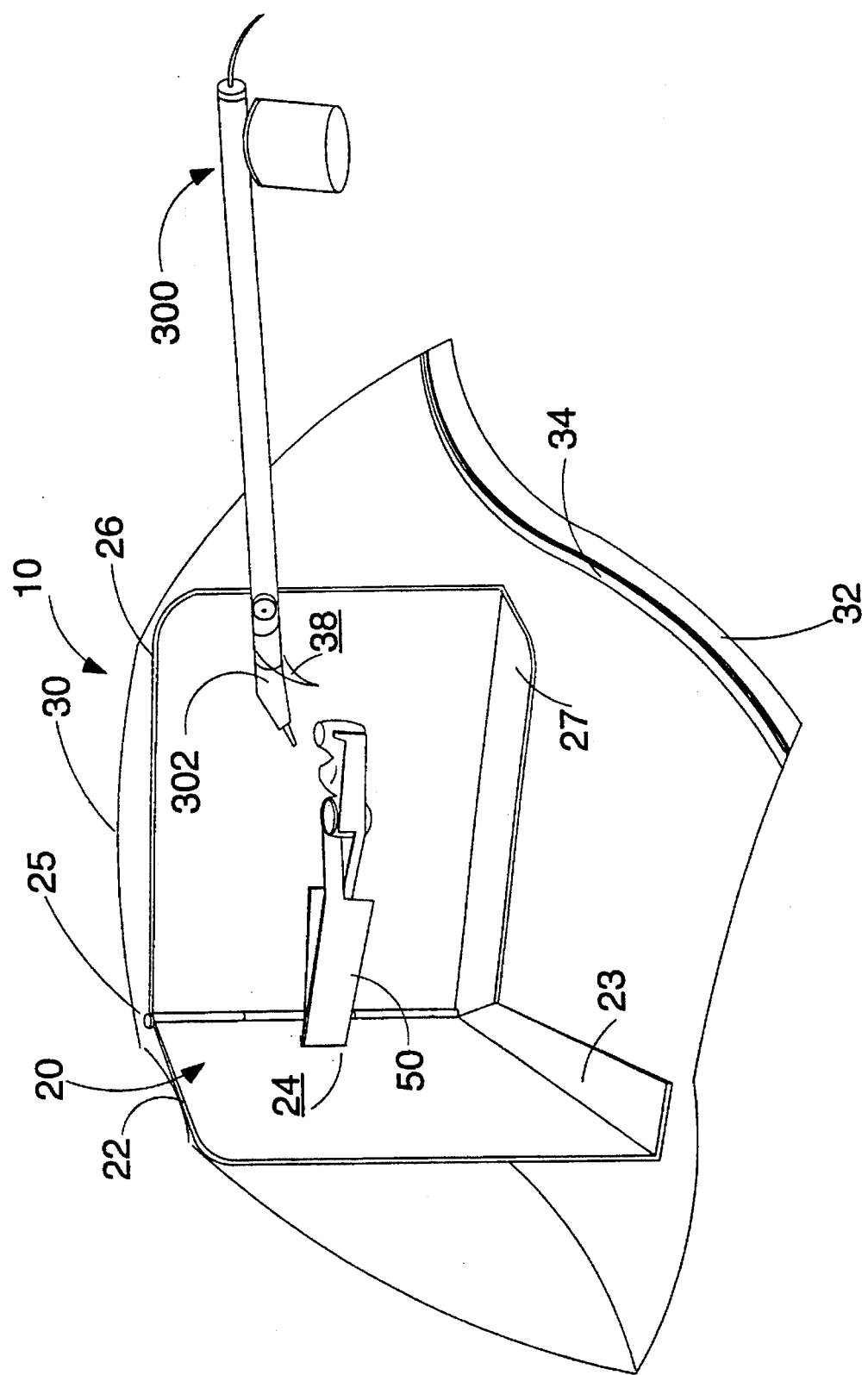
FIG. 1 is a perspective view of apparatus supporting and containing a dental prosthesis in accordance with the present invention.

Apparatus 10 in FIG. 1 consists of a framework generally designated 20 with two segments 22,26 connected by a hinge 25, a transparent, flexible enclosing hood 30, and a holder or clip 50 mounted to the framework. Framework 20 is shown in an open working position which holds hood 30 away from contact with the prosthesis or bridgework 200, the bridgework being releasably held by clip 50.

Figure 4:
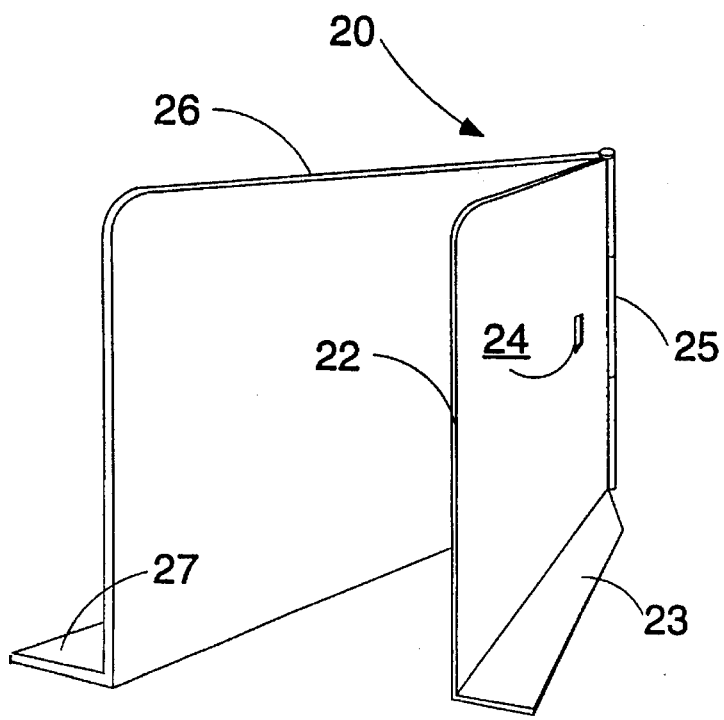
FIG. 4 is a perspective view of the framework in the apparatus of FIG. 1 when folded to a closed storage position.
Figure 5:
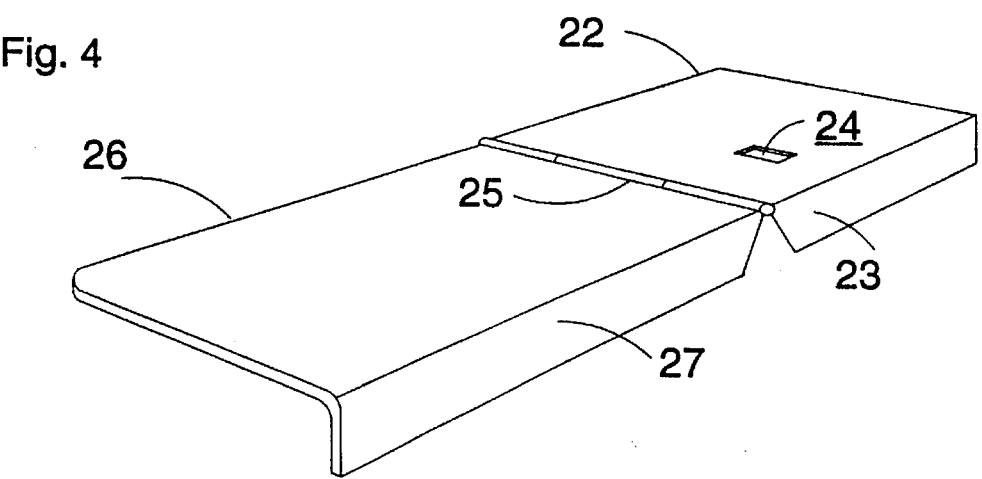
FIG. 5 is a perspective view of the framework in the apparatus of FIG. 1 in a fully extended position.

Framework 20 and its structural characteristics can be better seen in FIGS. 3, 4 and 5. In the open working position shown in FIG. 1, but as better seen in FIG. 3, flange 23 of segment 22 and flange 27 of segment 26 abut each other to establish the working position with an inner angle of about 90° between the segments. Further, flanges 23,27 serve to provide added strength and stability to the apparatus.

FIG. 4 illustrates framework 20 in a compact storage position where segment 22 has been swung backward around hinge 25 almost 270° from the open working position shown in FIG. 3.

FIG. 5 illustrates framework 20 in a position where segment 22 has been swung back about 90° from the open working position shown in FIG. 3 to a fully extended position. Like the position shown in FIG. 4, the extended position shown in FIG. 5 may serve as a relatively compact storage position - occupying more length but less depth than the position shown in FIG. 4. But, the extended position is also a good position to facilitate wiping and cleaning, or to facilitate sterilization in a relatively shallow sterilizing bath.

Segment 22 of framework includes a slot 24 which is sized to receive end portion 52 (see FIG. 6) of clip 50. Clip 50 is a standard spring clip, modified with the provision of a rectangular groove 54 in end portion 52. The width of groove 54 is toleranced marginally greater than the wall thickness of segment 22 thereby permitting the clip to be removably attached in slot 24 to the segment. Such removability facilitates storage, cleaning and replacement.

The positioning of slot 24 is not critical in any absolute sense. But, with reference to FIG. 1, and given the relative lengths of segments 22,26, and clip 50, it is positioned in the lower right quadrant of segment 22 to better avoid the drape of hood 30.

As best seen in FIG. 2, hood 30 includes an open end 32 which is sized to slidably receive framework 20 into the hood while holding prosthesis 200 in position for micro-etching. A sealing means comprising an upper sealing strip 34 and an opposed lower sealing strip 36 is carried by the hood near end 32. Upper strip 34 releasably engages and forms a seal with lower strip 36 when the two strips are pressed together as shown in FIG. 1.

All such features of hood 30 may be found in a standard transparent ZIPLOC® plastic bag, ZIPLOC being a trademark of The Dow Chemical Company. On such bags, one of strips 34,36 has an elongated ridge which runs the length of the strip and press fits with a corresponding elongated groove which runs the length of the opposed strip. Once fitted, a seal is formed, but the strips can be separated and the bag reopened with a small pulling force on the seal. The one alteration to a standard ZIPLOC bag which is needed for the present invention is the provision of a small slit 38 as shown in FIG. 1. As can be seen in FIG. 1, slit 38 permits tip 302 of micro-etching tool 300 to extend into the bag for the purpose of micro-etching. Although the slit may be made beforehand, it has been found more expedient to make a suitable cut with a knife edge once the framework with the attached clip and prosthesis are in the bag. Then, it is unnecessary to adjust the bag on framework 20 to locate the slit in a suitable position relative to the framework and prosthesis 200.

In principle, it may be possible to clean and sterilize ZIPLOC bags once they have been used during the micro-etching of a prosthesis. However, within the context of the present invention, such bags are considered to be low cost disposable items Following usage, the task of cleaning or sterilization is probably not justified by the time and cost.

In use, apparatus 10 as shown in FIG. 1 may rest on a desk or counter, or it may be hand held in one hand while the operator holds and manipulates tool 300 with the other. Regardless, however, the operator's hands or fingers will remain clear of the micro-etching environment within hood 30. Typically, this environment will be a higher pressure environment having a ballooning effect on the hood, but not so high as to produce any notable backflow of particles from the hood through slit 38.

Figure 7:
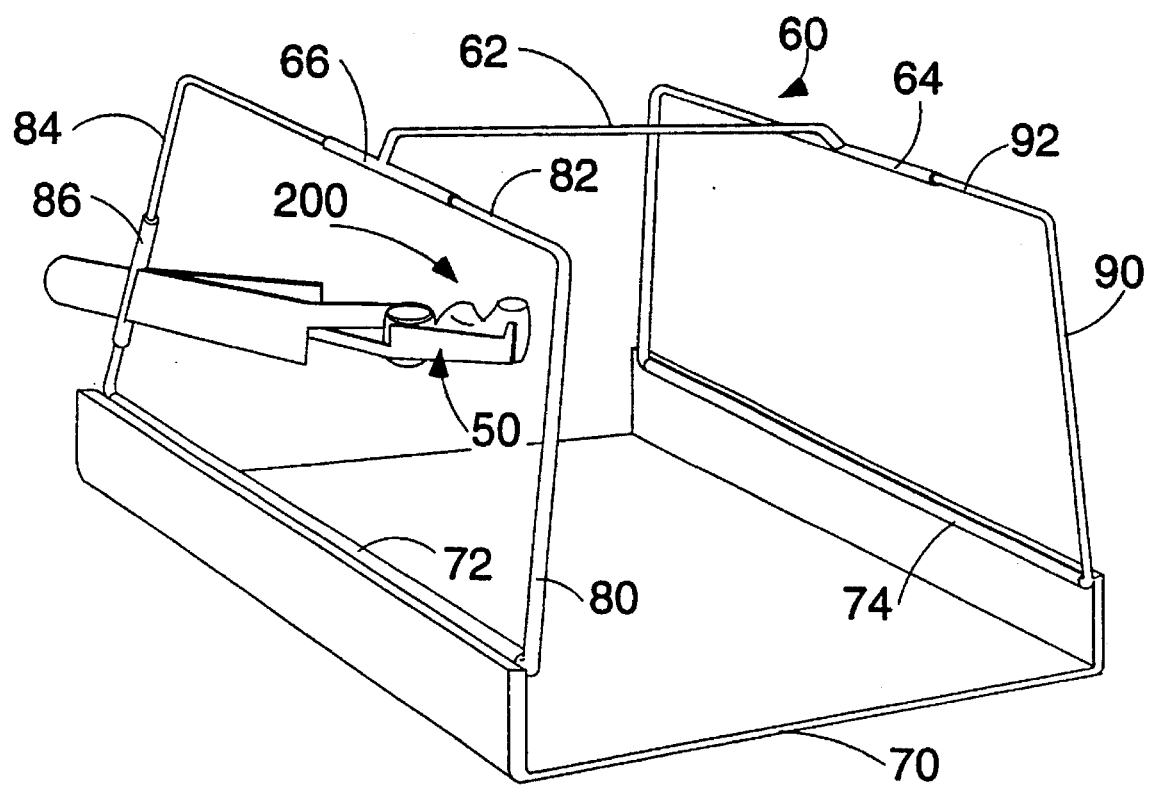
FIG. 7 is a perspective view of framework for an alternative embodiment of the present invention.

The design of framework 20 is a preferred design because it is particularly simple in structure and can be easily fabricated from metal plate. However a variety of other configurations are possible. By way of example, FIG. 7 illustrates an alternative embodiment of the present invention wherein a framework generally designated 60 makes extensive use of wire construction.

Framework 60 comprises a base frame 70 and a pair of opposed wire frame segments 80,90 hingedly mounted to base frame 70 by means of hinge sleeves 72,74. A separator arm 62 hingedly mounted to upper cross-arm 92 of segment 90 by means of hinge sleeve 64, and removably clipped by means of snap sleeve 66 to upper cross-arm 82 of segment 80, supports framework 60 in the working position shown in FIG. 7. FIG. 7 does not illustrate an enclosing flexible, transparent hood. However, such hood may be the same type of hood and used in the same manner as hood 30 described above.

Figure 6:
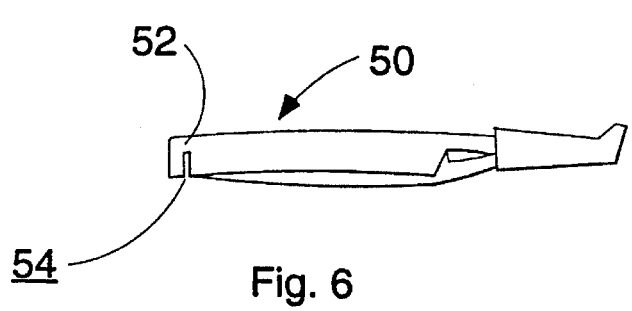
FIG. 6 is a more detailed view of the prosthesis holder clip in the apparatus of FIG. 1.

A prosthesis holding clip 50 having the same construction as clip 50 FIG. 6 is supported by framework 60 by means of hinge sleeve 86 on side arm 84 of segment 80. The curvature of arm 84 prevents sleeve 86 from sliding downwardly below the position shown in FIG. 7. Sleeve 86 includes a small projecting tab which is hidden from view but which serves to engage slot 54 and end portion 52 of clip 50. Clip 50, releasably gripping bridgework 200, is thus removably attached to framework 60.

The hinge mounting of clip 50 to framework 60 permits bridgework 200 to be rotated about side arm 84 when the apparatus is in use. For this purpose, it will be understood that the volume envelope described by the framework serves to hold the hood (not shown) away from contact with the bridgework over a significant angle of rotation. Such rotation, which is not possible with the embodiment of FIG. 1, allows for some added dexterity in the use of the apparatus. The operator can apply a finger grip to sleeve 86 or the clip (doing so through the thickness of the flexible hood) and then move bridgework 200 to a desired angle of rotation relative to the tip of a micro-etching tool.

Framework 60 can be collapsed to a more compact storage position by unsnapping sleeve 66 from cross-arm 82, then permitting frame segments 80, 90 to fold inwardly about their respective hinge sleeves 72, 74. Concurrently, separator arm 62 rotates about its hinge sleeve 64. In the collapsed condition framework 60 will fit easily within a relatively shallow sterilizing bath.

It will be readily apparent to those skilled in the art that a variety of modifications, changes and variations to the invention are possible within the spirit and scope of the claims which follow. The invention should not be considered as restricted to the specific embodiments described and illustrated with reference to the drawings.

We claim:

1. Apparatus for supporting and containing a dental prosthesis during the micro-etching thereof, said apparatus comprising:

(a) a framework;

(b) holding means carried by said framework for holding said prosthesis in a position permitting the micro-etching of said prosthesis;

(c) a flexible enclosing hood having an open end for slidably receiving said framework into said hood while holding said prosthesis in said micro-etching position, said framework being configured to hold said hood away from contact with said prosthesis while said framework is so received, said hood being transparent to permit viewing of said prosthesis within said hood; and, (d) means for sealing said open end while said framework is so received, said hood being sliceable with a knife edge to provide a small slit for permitting the tip of a micro-etching tool to extend into said hood for the micro-etching of said prosthesis while said framework is so received.

2. Apparatus as defined in claim 1, wherein said hood is a disposable plastic bag, the said open end of which is releasably sealable.

3. Apparatus as defined in claim 2, wherein said holding means comprises a holder for releasably gripping said prosthesis and means for removably attaching said holder to said framework.

4. Apparatus as defined in claim 1, wherein said framework is collapsible between an open working position and a storage position.

5. Apparatus as defined in claim 1, wherein said framework comprises a first segment for carrying said holding means and a second segment hingedly connected with said first segment, said hinge connection permitting said segments to be folded between an open working position and a storage position.

6. Apparatus as defined in claim 5, wherein said holding means comprises a holder for releasably gripping said prosthesis and means for removably attaching said holder to said first segment.

7. Apparatus as defined in claim 1, wherein said holding means comprises a holder for releasably gripping said prosthesis, said holder being rotatably mounted to said framework.

8. Apparatus for supporting and containing a dental prosthesis during the micro-etching thereof, said apparatus comprising:

(a) a framework;

(b) holding means carried by said framework for holding said prosthesis in a position permitting the micro-etching of said prosthesis;

(c) a flexible enclosing hood having an open end for slidably receiving said framework into said hood while holding said prosthesis in said micro-etching position, said framework being configured to hold said hood away from contact with said prosthesis while said framework is so received, said hood being transparent to permit viewing of said prosthesis within said hood, said hood including a thin slit for permitting the tip of a micro-etching tool to extend into said hood for the micro-etching of said prosthesis while said framework is so received; and, (d) means for sealing said open end while said framework is so received.

9. Apparatus as defined in claim 8, wherein said hood is a disposable plastic bag, the said open end of which is releasably sealable.

10. Apparatus as defined in claim 9, wherein said holding means comprises a holder for releasably gripping said prosthesis and means for removably attaching said holder to said framework.

11. Apparatus as defined in claim 8, wherein said framework is collapsible between an open working position and a storage position.

12. Apparatus as defined in claim 8, wherein said framework comprises a first segment for carrying said holding means and a second segment hingedly connected with said first segment, said hinge connection permitting said segments to be folded between an open working position and a storage position.

13. Apparatus as defined in claim 12, wherein said holding means comprises a holder for releasably gripping said prosthesis and means for removably attaching said holder to said first segment.

14. Apparatus as defined in claim 8, wherein said holding means comprises a holder for releasably gripping said prosthesis, said holder being rotatably mounted to said framework.

* * * * *